(12) United States Patent
Sendai

(10) Patent No.: US 7,613,276 B2
(45) Date of Patent: *Nov. 3, 2009

(54) MAMMOGRAPHY APPARATUS

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/543,951

(22) Filed: Oct. 6, 2006

(65) Prior Publication Data

US 2007/0081625 A1    Apr. 12, 2007

(30) Foreign Application Priority Data

| Oct. 6, 2005 | (JP) | ............................. 2005/293789 |
| Mar. 27, 2006 | (JP) | ............................. 2006/084366 |
| Oct. 3, 2006 | (JP) | ............................. 2006/271420 |

(51) Int. Cl.
*A61B 6/04* (2006.01)
(52) U.S. Cl. ......................................... 378/37; 378/97
(58) Field of Classification Search ................... 378/37, 378/4–27, 96, 97, 108, 208
See application file for complete search history.

(56) References Cited

U.S. PATENT DOCUMENTS

| 5,142,557 A | 8/1992 | Toker et al. |
| 5,627,869 A | 5/1997 | Andrew et al. ................. 378/37 |
| 2003/0016778 A1 | 1/2003 | Tachizaki et al. .............. 378/4 |
| 2004/0101095 A1 | 5/2004 | Jing et al. ...................... 378/37 |
| 2005/0063509 A1 | 3/2005 | Defreitas et al. .............. 378/37 |
| 2005/0087694 A1 | 4/2005 | Shoji |
| 2005/0195938 A1 | 9/2005 | Zetterlund |
| 2007/0121782 A1* | 5/2007 | Sendai ......................... 378/37 |

FOREIGN PATENT DOCUMENTS

| EP | 1525846 A1 | 4/2005 |
| JP | 4-9145 A | 1/1992 |
| JP | 08-033621 | 2/1996 |
| JP | 08-238237 | 9/1996 |
| WO | WO 01/54463 A1 | 7/2001 |
| WO | 03/010555 A2 | 2/2003 |
| WO | 2004/049949 A1 | 6/2004 |

* cited by examiner

*Primary Examiner*—Courtney Thomas
(74) *Attorney, Agent, or Firm*—Sughrue Mion, PLLC

(57) ABSTRACT

A mammography apparatus capable of obtaining a breast image having an optimum density with reduced burden on the subject. The apparatus includes a radiation irradiation section and an object table connected to an arm such that they face each other, and the breast compressed onto the object table using a compression paddle is imaged by rotating the arm by an arm rotation means according to the imaging direction. In the apparatus, the size of the breast is detected, and the position of a dose detector is moved along the side of the object table facing the chestwall of the subject according to the detected size of the breast and the angle of rotation of the arm when rotated by the arm rotation means.

23 Claims, 14 Drawing Sheets

| BODY HEIGHT (cm) | HEIGHT OF IMAGING PLATFORM (cm) | DISPLACEMENT (cm) |
|---|---|---|
| 140 | 106 | 30 |
| 145 | 108 | 30 |
| 150 | 110 | 24 |
| 155 | 112 | 18 |
| 160 | 113 | 14 |
| 165 | 118 | 10 |
| 170 | 122 | 5 |
| 175 | 126 | 0 |
| 180 | 130 | 0 |

MAMMOGRAPHY APPARATUS

BACKGROUND OF THE INVENTION

1. Field of the Invention

The present invention relates to a mammography apparatus for obtaining a breast image.

2. Description of the Related Art

Breast cancer screenings are conducted using X-ray machines dedicated to breast imaging (mammography apparatus), since the discovery rate of early stage cancer is increased by combining mammograms obtained by the mammography apparatus with clinical breast examinations rather than depending only on the clinical breast examinations.

General breast cancer screenings include a unidirectional imaging (two images) and a two-directional imaging (four images). In the unidirectional imaging, only the MLO (mediolateral oblique) imaging is conducted. In the MLO imaging, the breast is clamped and imaged from the oblique direction so that the greater pectoral muscles are imaged as shown in FIG. 14A. In order to enable the imaging from such direction, the mammography apparatus includes an arm to which a radiation irradiation section and an object table are connected such that they face each other, and the object table is inclined by rotating the arm. In the two-directional imaging, both the MLO imaging and CC (craniocaudal) imaging are conducted. In the CC imaging, the breast is clamped and imaged from above as shown in FIG. 14B. The MLO imaging may provide an image having the widest area of a breast. The CC imaging is performed to complement the MLO imaging, since it may visualize inside areas of a breast which are difficult for the MLO imaging to visualize as an image. Generally, a unidirectional imaging and a two-directional imaging is performed for each of the right and left breasts, and two images are obtained in the unidirectional imaging and four images are obtained in the two-directional imaging.

The breast includes mammary gland tissues, fat tissues and skin. In order to obtain a breast image required for giving an accurate diagnosis, the breast needs to be compressed evenly as much as possible to image small mammary glands and fat tissues on a film. Therefore, in the mammography apparatus, the breast is imaged while it is clamped between the object table and a compression paddle. If the pressing pressure is too low, however, the mammary glands, fat, blood vessels and the like overlap with each other. Consequently, there may be a case in which a tumor actually existing in the breast is not imaged. Thus, in order to obtain a good image, the breast needs to be compressed to a certain extent when imaged. That is, the pressing pressure needs to be controlled such the thickness of the breast becomes appropriate for imaging for each type of breast.

Further, AEC (automatic exposure control) for measuring the dose of radiation transmitted through the breast is essential in order to stably obtain an appropriate film density by the mammography apparatus. The AEC is a sensor provided under the cassette, and in general, semiconductor detectors are disposed as the sensor. When imaging a breast of a subject, the position of the breast and the like are adjusted by the operator so that the dose of radiation irradiated on the center of the breast is measured by the sensor.

Therefore, when the two-directional imaging is performed for the right and left breasts of a subject, such adjustments are required to be made four times, causing a considerable burden on the subject.

Consequently, a mammography apparatus, in which an initially adjusted pressing pressure value or the like for each subject is stored for repeatedly performed mammography screening, and imaging is performed using the stored value from the next time, is proposed as described, for example, in International Patent Publication No. WO01/054463.

Further, in order to obtain an image having an optimum density, it is necessary to place the breast on the object table that includes AEC such that the center of the breast corresponds to the center of the object table so that the dose of X-rays transmitted through the central portion of the breast is detected. The size of the breast, however, varies greatly between individuals, so that a large object table is used for imaging a large breast, and a small object table is used for imaging a small breast so that the breast is placed on the center of the object table in the apparatus proposed in the aforementioned patent publication.

The burden on the subject may be alleviated by storing information related to the pressing pressure and the like as proposed in the aforementioned patent publication, but it is difficult to invariably place the breast on the center of the object table. Consequently, there may be a case that the density of the image is inappropriate.

Further, the size of the breast varies greatly between individuals, and if a small breast is imaged using a large object table, the position of the breast may be displaced from the center of the object table, so that it is desirable to use object tables of different sizes according to the size of the breast. But, the object table having a flat panel detector accommodated therein is expensive, so that it may be difficult to invariably provide both the large and small platforms.

Consequently, when a small breast is imaged using a large object table, the dose of radiation detected by the AEC sensor is not always the dose of radiation transmitted through the central portion of the breast. This may result in the image having an inappropriate density.

Further, use of a large platform for imaging a small breast causes a problem that it is hard for the operator to withdraw its hand after positioning the breast.

It is an object of the present invention, therefore, to provide a mammography apparatus capable of automatically obtaining a breast image having an optimum density with reduced burden on the subject.

SUMMARY OF THE INVENTION

A first mammography apparatus of the present invention includes:

a radiation irradiation section for irradiating radiation on a breast of a subject;

an object table having therein an image recording medium that receives the radiation to record image information thereon according to the dose of radiation transmitted through the breast, and a dose detector for detecting the dose of radiation irradiated from the radiation irradiation section and transmitted through the breast;

an arm connecting the radiation irradiation section and object table such that they face each other;

a compression paddle, disposed between the radiation irradiation section and object table, for compressing the breast onto the object table;

an arm rotation means for rotating the arm according to the imaging direction for the breast;

a breast size detection means for detecting the size of the breast of the subject; and a dose detecting position changing means for changing the dose detecting position of the dose detector along the side of the object table facing the chest wall of the subject according to the detected size of the breast and the direction of rotation of the arm when rotated by the arm rotation means.

The referent of "image recording medium" as used herein means a medium on which an image of a subject through which radiation has transmitted is recorded. Specifically, such media include flat panel detectors, imaging plates, X-ray films, and the like. The flat panel detectors include solid state detectors, TFTs (thin film transistors), and the like.

The referent of "side of the object table facing the chest wall" as used herein means the side of the object table that faces the chest wall when imaging the breast, and the referent of the "changing the position of the dose detector along the side of the object table facing the chest wall" as used herein means that the position of the dose detector is changed substantially parallel to the side of the object table facing the chest wall.

The first mammography apparatus may further includes a compression paddle compressing position moving means for moving the compressing position of the compression paddle along the side of the object table facing the chest wall of the subject according to the detected size of the breast and the direction of rotation of the arm when rotated by the arm rotation means.

The first mammography apparatus may further include a compression paddle size detection means for detecting the size of the compression paddle. Here, the breast size detection means may be a means for detecting the size of breast corresponding to the detected size of the compression paddle as the size of the breast of the subject.

The dose detecting position changing means may include a first switching means for switching whether to move the dose detecting position of the dose detector according to the detected size of the compression paddle.

A second mammography apparatus of the present invention includes:

a radiation irradiation section for irradiating radiation on a breast of a subject;

an object table having therein an image recording medium that receives the radiation to record image information thereon according to the dose of radiation transmitted through the breast, and a dose detector for detecting the dose of radiation irradiated from the radiation irradiation section and transmitted through the breast;

an arm connecting the radiation irradiation section and object table such that they face each other;

a compression paddle, disposed between the radiation irradiation section and object table, for compressing the breast onto the object table;

an arm rotation means for rotating the arm according to the imaging direction for the breast;

a breast size detection means for detecting the size of the breast on the object table; and a compression paddle compressing position moving means for moving the compressing position of the compression paddle along the side of the object table facing the chest wall of the subject according to the detected size of the breast and the angle of rotation of the arm when rotated by the arm rotation means.

The second mammography apparatus may further includes a compression paddle size detection means for detecting the size of the compression paddle. Here, the breast size detection means may be a means for detecting the size of breast corresponding to the detected size of the compression paddle as the size of the breast of the subject.

The compression paddle compressing position moving means may include a second switching means for switching whether to move the compressing position of the compression paddle according to the detected size of the compression paddle.

Further, the breast size detection means may be a means for detecting the size of the breast of the subject from the image information recorded on the image recording medium.

A third mammography apparatus of the present invention includes:

a radiation irradiation section for irradiating radiation on a breast of a subject;

an object table for placing the breast thereon;

a breast position detection means for detecting the position of the breast on the object table along the side of the object table facing the chest wall of the subject;

a radiation dose measuring means for measuring the dose of radiation irradiated from the radiation irradiation section and reached the object table at a position on the straight line passing through the radiation irradiation section and region of interest of the breast based on the position of the breast detected by the breast position detection means.

The referent of "region of interest" as used herein means the region around which radiation is irradiated when a breast image is recorded. When imaging a breast, it is desirable that the radiation is irradiated centered on the region of the breast where it is relatively thick. For example, the central region of the breast may be the region of interest.

The radiation dose measuring means may be a means that includes: a plurality of dose detectors arranged along the side of the object table facing the chest wall; and a dose detecting position selection means for selecting the dose detector located on the straight line passing through the radiation irradiation section and region of interest of the breast.

Further, the radiation dose measuring means may be a means that includes: a dose detector provided movably along the side of the object table facing the chest wall; and a dose detecting position changing means for changing the dose detecting position by moving the dose detector to a position on the straight line passing through the radiation irradiation section and region of interest of the breast.

The third mammography apparatus may further include: an arm connecting the radiation irradiation section and object table such that they face each other; an arm rotation means for rotating the arm according to the imaging direction for the breast; and a breast size detection means for detecting the size of the breast on the object table. Here, the breast position detection means may be a means for detecting the position of the breast on the object table according to the angle of rotation of the arm when rotated by the arm rotation means and the size of the breast.

Further, the third mammography apparatus may further includes an object table height adjusting means for adjusting the height of the object table. Here, the breast position detection means may be a means for determining the position of the breast on the object table according to the height of the object table adjusted by the object table height adjusting means.

Further, the third mammography apparatus may further includes: a compression paddle, disposed between the radiation irradiation section and object table, for compressing the breast onto the object table; and a compression paddle inclination detection means for detecting an inclination angle of the compression paddle formed with respect to the object table while the breast is clamped between the compression paddle and the object table and compressed. Here, the breast position detection means may be a means for determining the position of the breast on the object table according to the inclination angle of the compression paddle.

Still further, the third mammography apparatus may further includes a radiation field aperture detection means for detecting the position where a radiation field aperture for the radiation irradiation section is attached. Here, the breast position detection means may be a means for determining the position of the breast on the object table according to the position of the radiation field aperture.

A fourth mammography apparatus of the present invention includes:

a radiation irradiation section for irradiating radiation on a breast of a subject;

an object table for placing the breast thereon;

an arm connecting the radiation irradiation section and object table such that they face each other;

a compression paddle, disposed between the radiation irradiation section and object table, for compressing the breast onto the object table;

a breast position detection means for detecting the position of the breast on the object table along the side of the object table facing the chest wall of the subject; and a compression paddle compressing position moving means for moving the compressing position of the compression paddle along the side of the object table facing the chest wall of the subject based on the position of the breast detected by the breast position detection means.

The fourth mammography apparatus may further includes: an arm rotation means for rotating the arm according to the imaging direction for the breast; and a breast size detection means for detecting the size of the breast on the object table. Here, the breast position detection means may be a means for detecting the position of the breast on the object table according to the angle of rotation of the arm when rotated by the arm rotation means and the size of the breast.

The fourth mammography apparatus may further includes an object table height adjusting means for adjusting the height of the object table. Here, the breast position detection means may be a means for determining the position of the breast on the object table according to the height of the object table adjusted by the object table height adjusting means.

Further, the fourth mammography apparatus may further includes a compression paddle inclination detection means for detecting an inclination angle of the compression paddle formed with respect to the object table while the breast is clamped between the compression paddle and the object table and compressed. Here, the breast position detection means may be a means for determining the position of the breast on the object table according to the inclination angle of the compression paddle.

Still further, the fourth mammography apparatus may further includes a radiation field aperture detection means for detecting the position where a radiation field aperture for the radiation irradiation section is attached. Here, the breast position detection means may be a means for determining the position of the breast on the object table according to the position of the radiation field aperture.

According to the present invention, the detecting position of the dose detector is moved according to the size of the breast to be imaged such that the detecting position corresponds to the central portion of the breast. Thus, an image having an appropriate density may be obtained with minimum exposure of radiation to the subject.

Further, the size of the breast may be readily detected by detecting the size of the compression paddle.

Still further, by detecting the size of the breast from the image information, the center of the breast may be detected accurately, and thereby the dose of radiation may be detected at a more appropriate position.

Further, the breast may be compressed evenly by moving the position of the compression paddle according to the size of the breast, and pressing the breast at an appropriate position. Thus, a breast image appropriate for diagnosis may be obtained.

Still further, the position of the breast on the object table may be determined without requiring any structural change in the mammography apparatus by determining the position of the breast from the height of the object table.

Further, the position of the breast being compressed onto the object table may be determined by determining the position of the breast from the inclination angle of the compression paddle.

Still further, the position of the breast on the object table may be readily determined by determining the position of the breast according to the position where the radiation field aperture is attached with the center of imaging as the center of the breast.

DESCRIPTION OF THE PREFERRED EMBODIMENTS

Figure 1:
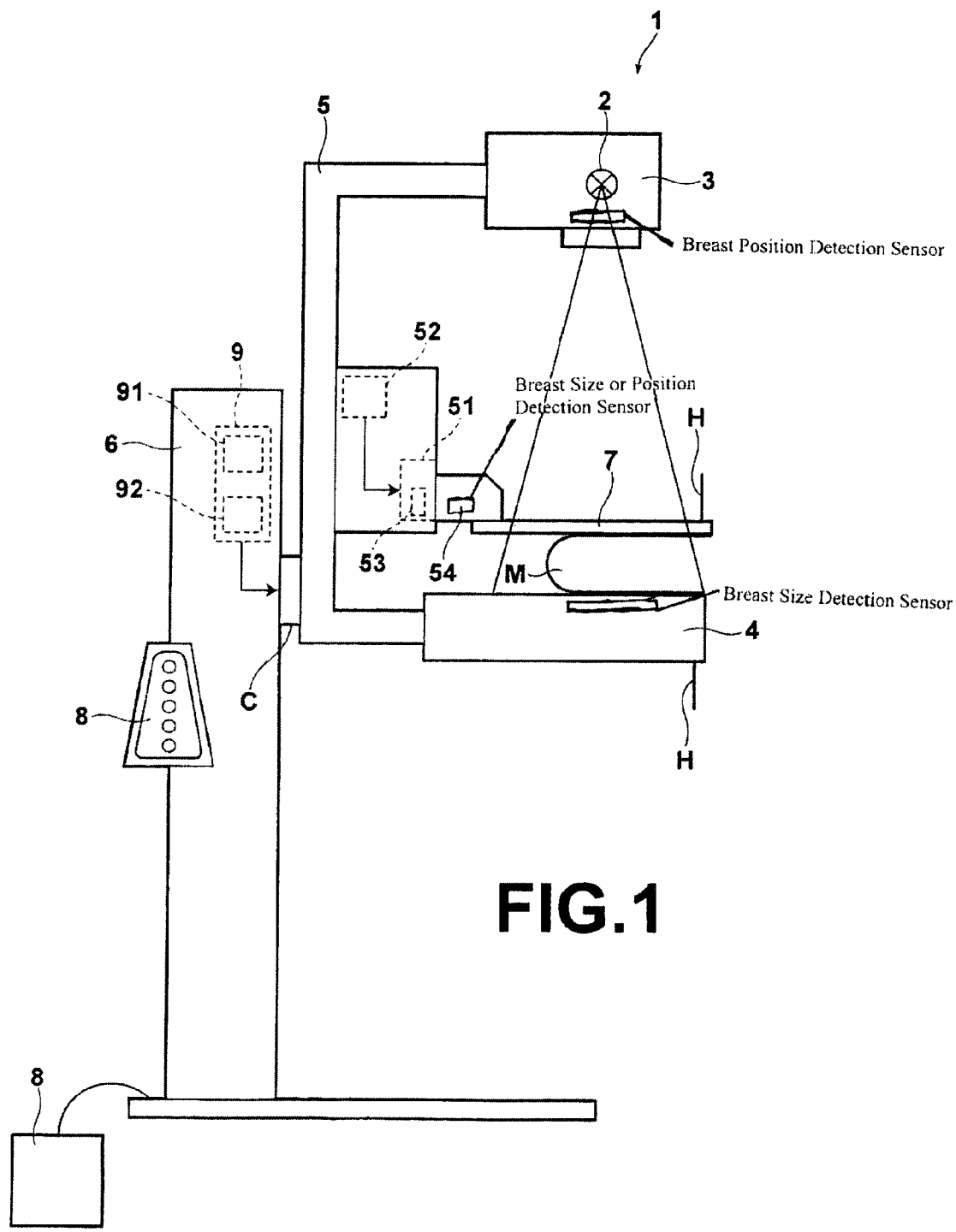
FIG. 1 is a schematic view of the mammography apparatus according to a first embodiment of the present invention.
Figure 2:
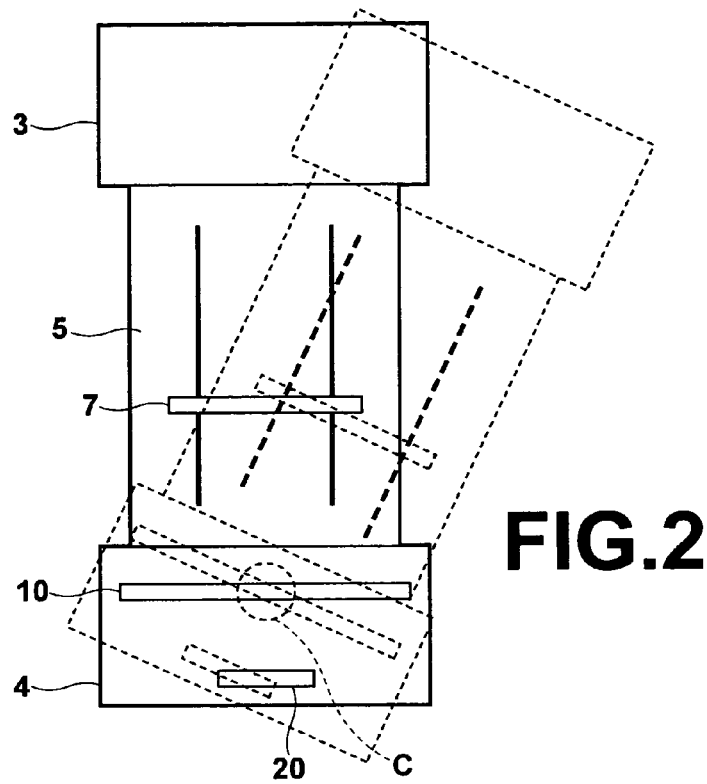
FIG. 2 is a front view of the arm section of the mammography apparatus.

Hereinafter, exemplary embodiments of the present invention will be described with reference to the accompanying drawings. FIG. 1 is a schematic view of the mammography apparatus according to a first embodiment of the present invention, and FIG. 2 is a front view of the arm section of the mammography apparatus.

The mammography apparatus 1 includes: a radiation irradiation section 3 having therein a radiation source 2; an object table 4 having therein a recording medium holding section, such as a cassette or the like, in which a recording medium, such as a flat panel detector 10 or the like is accommodated; an arm 5 connecting the radiation irradiation section 3 and object table 4 such that they face each other. The arm 5 is attached to a base 6 through a spindle C.

The base 6 further includes: an operation section 8 for use by the operator to control the height of the platform 4 (i.e., height of the arm 5), and inclination of the platform 4 (i.e., inclination of the arm 5); and an arm moving means 9 for vertically and rotationally moving the arm 5 according to the input from the operation section 8.

The operation section 8 is constituted by an operation panel, a foot pedal, and the like attached to the base 6 for use by the operator to input instructions for changing the height and orientation of the arm 5 to a position appropriate for imaging according to the physical size, breast size and position of a subject, and to input instructions for compressing the breast. For example, when a button on the operation panel is depressed once by the operator, information indicating the amount of vertical or rotational movement determined by the depression of the button is sent to the arm moving means 9, which controls the vertical and rotational movement of the arm 5 according to the received information.

The arm moving means 9 includes: an arm rotation means 91 for rotating the arm 5; and an arm height adjusting means (object table height adjusting means) 92 for adjusting the height of the object table 4 by moving the arm 5 up and down.

The arm rotation means 91 rotates the spindle C attached to the base 6 according to the inclination of the arm 5 inputted from the operation section 8.

The object table adjusting means 92 moves the arm 5 up or down according to the height of the object table inputted from the operation section 8.

The arm moving means 9 includes therein a travel distance recording section (not shown) for recording the travel distance of the arm 5 moved through the control operation by the operator, and the vertical distance and angle of rotation from the home position are recorded.

Between the radiation irradiation section 3 and object table 4, the arm 5 includes: a mounting section 51 for mounting a compression paddle 7 used for compressing a breast M onto the object table 4 from above; a compression paddle moving means 52 for moving the mounting section 51 up and down along the vertical direction of the arm 5; and a compression paddle size detection means 53 for detecting the size of the mounted compression paddle 7. In the mean time, the compression paddle 7 includes an insertion section 54, which is inserted into the mounting section 51 of the arm 5.

A plurality of compression paddles 7 of different sizes is provided for breasts of different sizes. The size of the large compression paddle 7 is approximately 30 cm×24 cm, and the size of the small compression paddle 7 is approximately 24 cm×18 cm. Further, the length of the insertion section 54 of the compression paddle 7 differs according to the size of the compression paddle 7.

The compression paddle size detection means 53 is provided on the mounting section 51 of the arm 5, which includes a dip switch or a photo sensor that detects the length of the insertion section 54 inserted into the mounting section 51 to detect the size of the compression paddle 7. Alternatively, it may be a barcode reader, in which case a barcode indicating the size or model number of the compression paddle 7 is attached to the side thereof, and the barcode reader is placed at a position so that the barcode may be scanned by the barcode reader when the compression paddle 7 is inserted into the mounting section 51.

Figure 3:
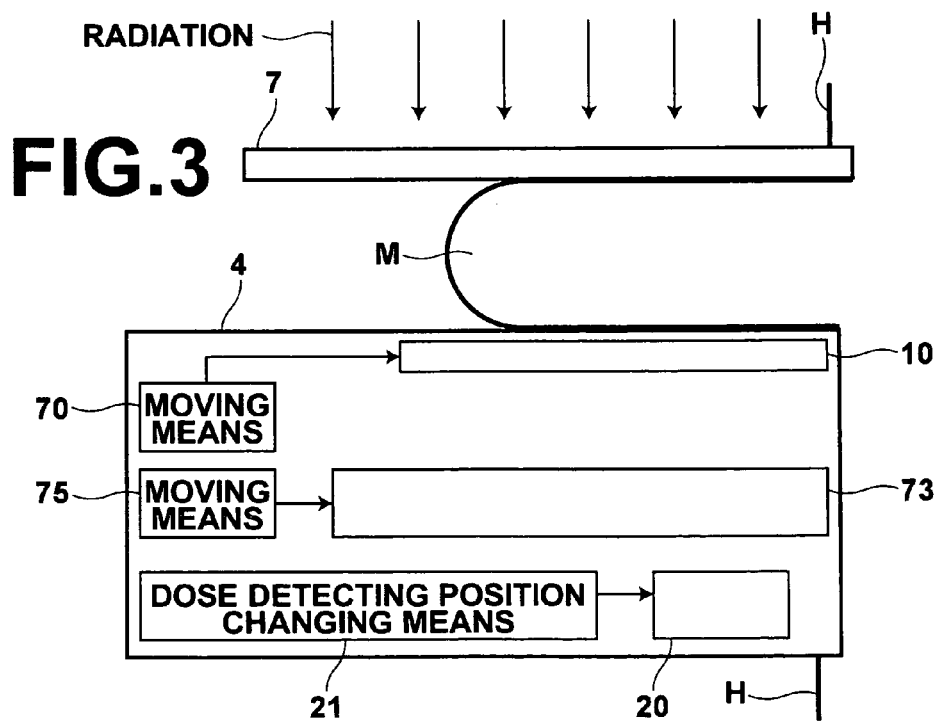
FIG. 3 is a drawing illustrating the relationship among the compression paddle, solid state detector, and dose detector (example 1).

Arranged inside of the object table 4 are: a flat panel detector 10, which is a solid state detector that receives the radiation irradiated from the radiation irradiation section to record image information according to the dose of radiation transmitted through the breast, and outputs image data representing the recorded image information; and a radiation dose measuring means, which is disposed under the flat panel detector 10, for detecting the dose of radiation transmitted through the breast and reached the object table 4 as shown in FIG. 3.

The radiation dose measuring means includes: a dose detector 20 disposed under the flat panel detector 10 and detects dose of radiation irradiated from the radiation irradiation section 3 and transmitted through the breast; and a dose detecting position changing means 21 for changing the position of the dose detector 20 to the center of the breast.

The arm 5 is attached to the base 6 through the spindle C, the rotation center of the arm 5, attached to the arm at a position corresponding to the center of the flat panel detector 10 so that the rotation center of the arm 5 corresponds to the center of the flat panel detector 10 (FIG. 2).

Hereinafter, the construction of the object table 4 when a solid state detector is used as the flat panel detector 10 will be described with reference to FIGS. 4 to 7.

Figure 4:
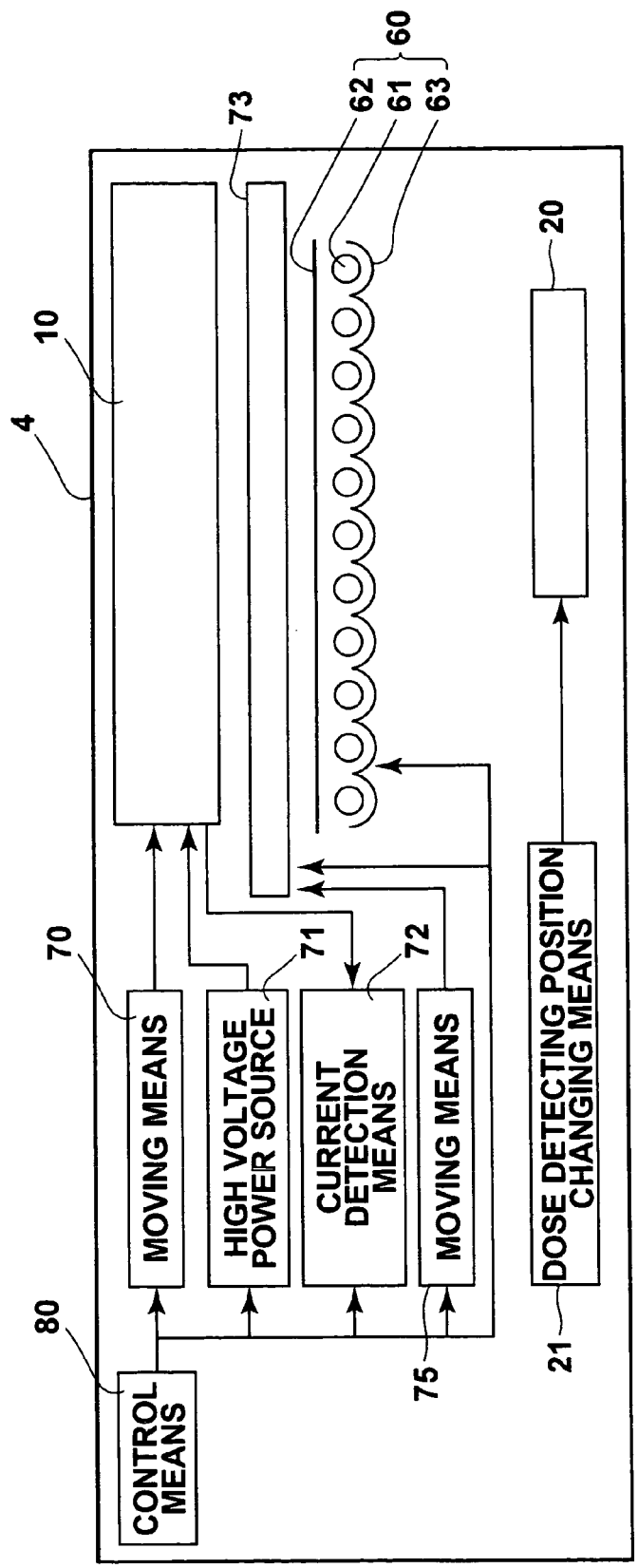
FIG. 4 is a schematic diagram of the object table of the mammography apparatus, illustrating the inside thereof.
Figure 5:
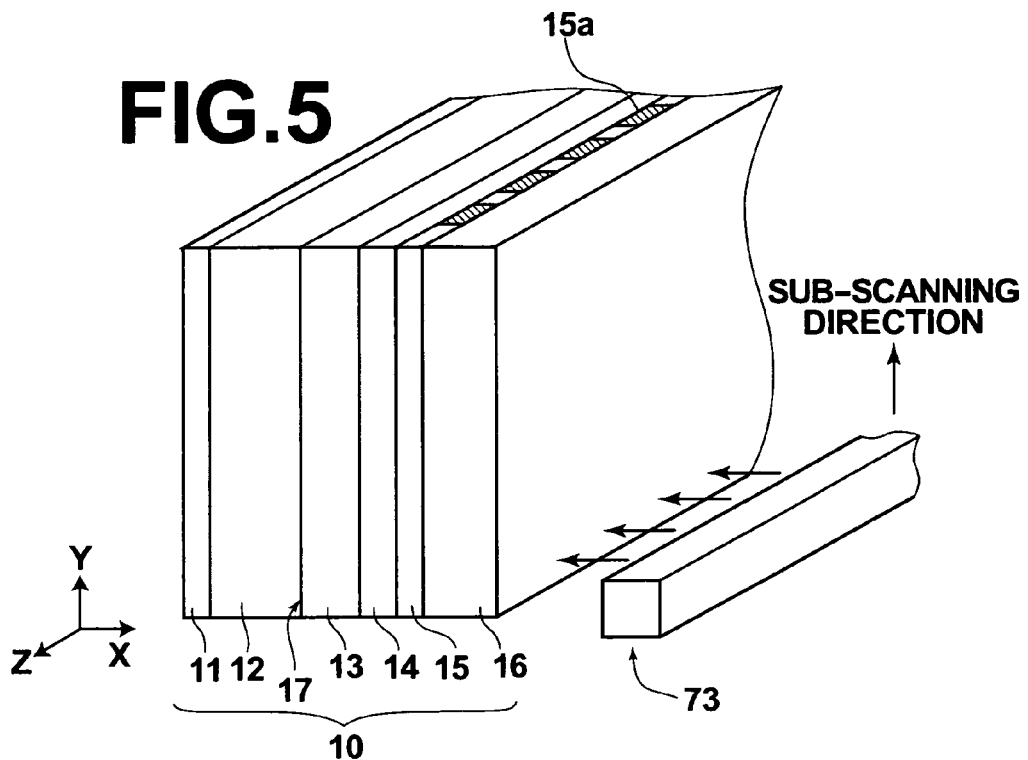
FIG. 5 is a schematic view of the solid state detector.

As shown in FIG. 4, arranged inside of the object table 4 are: a readout exposure light source section 73 used when reading out image information recorded on the solid state detector 10; a readout exposure light source section moving means 75 for moving the readout exposure light source section 73 in the sub-scanning directions; a current detection means 72 for detecting currents flowing out of the solid state detector 10 when scan exposed by the readout exposure light source section 73 to obtain image signals; a high voltage power source section 71 for applying a predetermined voltage to the solid state detector 10; a pre-exposure light source section 60 for irradiating pre-exposure light on the solid state detector 10 prior to initiating imaging; a solid state detector moving means 70 for moving the solid state detector 10 in the directions approaching the chest wall H of the subject and leaving therefrom (sub-scanning directions described above) within the object table 4; and a control means 80 for controlling the readout exposure light source section 73, current detection means 72, high voltage power source section 71, pre-exposure light source section 60, and moving means 70, 75. As would be apparent to one of skill in the art, the above discussed sections are implemented as computer controlled devices.

The solid state detector 10 is a direct conversion optical readout type solid state radiation detector, which receives recording light representing image information to record the image information as an electrostatic latent image, and is scanned by readout light to generate currents according to the electrostatic latent image. More specifically, as shown in FIG.

5, it includes a glass substrate on which the following are layered in the order listed below: a first conductive layer 11 which is transparent to the radiation(recording light) transmitted through a breast M; a recording photoconductive layer 12 that generates charges and shows electrical conductivity by receiving the recording light; a charge transport layer 13 that acts substantially as an insulator against charges having the polarity of latent image charges charged on the first conductive layer 11, and substantially as a conductor for transport charges having the opposite polarity to that of the latent image charges; a readout photoconductive layer 14 that generates charges and shows electrical conductivity by receiving readout light; and a second conductive layer 15 which is transparent to the readout light. In addition, a storage section 17 is formed at the interface between the recording photoconductive layer 12 and charge transport layer 13.

The first conductive layer 11 and second conductive layer 15 are electrode layers. The electrode of the first conductive layer 11 is a plate electrode which is two dimensionally flat, and the electrode of the second conductive layer 15 is a striped electrode constituted by multitudes of elements (line electrodes) 15a for detecting the recorded information as image signals arranged in stripes at a pixel pitch as shown in hatched lines in FIG. 5 (refer for example, to the electrostatic recording medium described in Japanese Unexamined Patent Publication No. 2000-105297 for detail). The arrangement direction of the elements 15a corresponds to the main scanning directions, and the longitudinal direction of the elements 15a corresponds to the subs-scanning directions.

The solid state detector 10 has a long side of 30 cm and a short side of 24 cm so as to be able to accept a large breast, and is arranged in the object table 4 such that the long side directions correspond to the main scanning directions and the short side directions correspond to the sub-scanning directions.

As for the readout exposure light source section 73, a light source constituted by a line light source having a plurality of LED chips arranged in a line, and an optical system for irradiating the light outputted from the line light source on the solid state detector 10 in a line. The entire surface of the solid state detector 10 is exposed by scanning the light source section 73 in the longitudinal direction of the striped electrodes of the detector 10, i.e., the sub-scanning directions by the moving means 75 constituted by a linear motor with a required distance between the light source section 73 and solid state detector 10 maintained. The readout exposure light source section 73 and the moving means 75 constitute the readout light scanning means.

Figure 6:
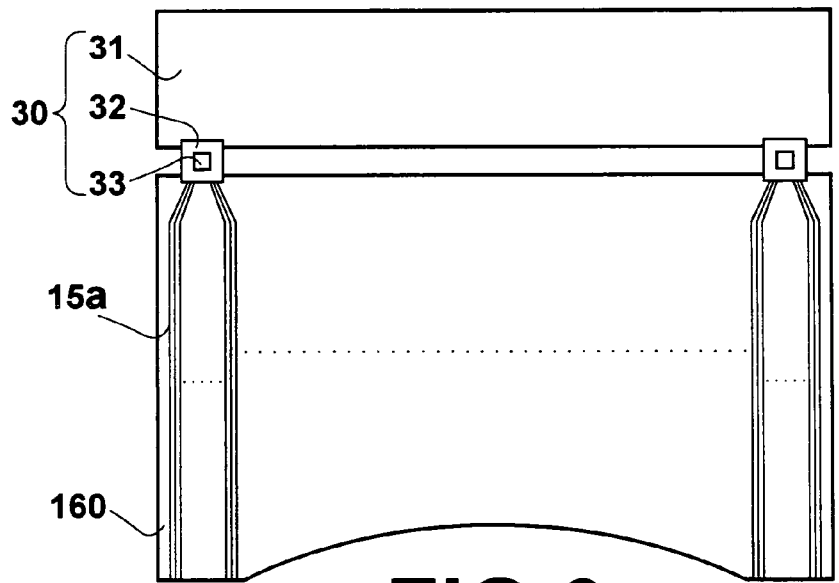
FIG. 6 is a drawing illustrating the solid state detector and the connection of the current detection means to the detector.

FIG. 6 is a drawing illustrating the solid state detector 10 and the connection of the current detection means 72 to the detector. As shown in the drawing, each element 15a is connected to a charge amplifier IC 33 through a printed pattern (not shown) formed on a TAB (tape automated bonding) film 32 on the side of the detector 10 to be contacted with the chest wall H of a subject. Further, the charge amplifier IC 33 is connected to a printed circuit board 31 through a printed pattern (not shown) formed on the TAB film 32. In the present embodiment, instead of connecting all of the elements 15a to a single charge amplifier IC 33, several to several tens of charge amplifiers are provided, and every several to several hundreds of elements 15a are connected to each charge amplifier IC 33.

The embodiment of the current detection means 72 is not limited to that described above, and it may be embodied as so-called COG (chip on glass) in which the charge amplifier ICs are formed on the glass substrate 16 instead of the TAB film 32.

Figure 7:
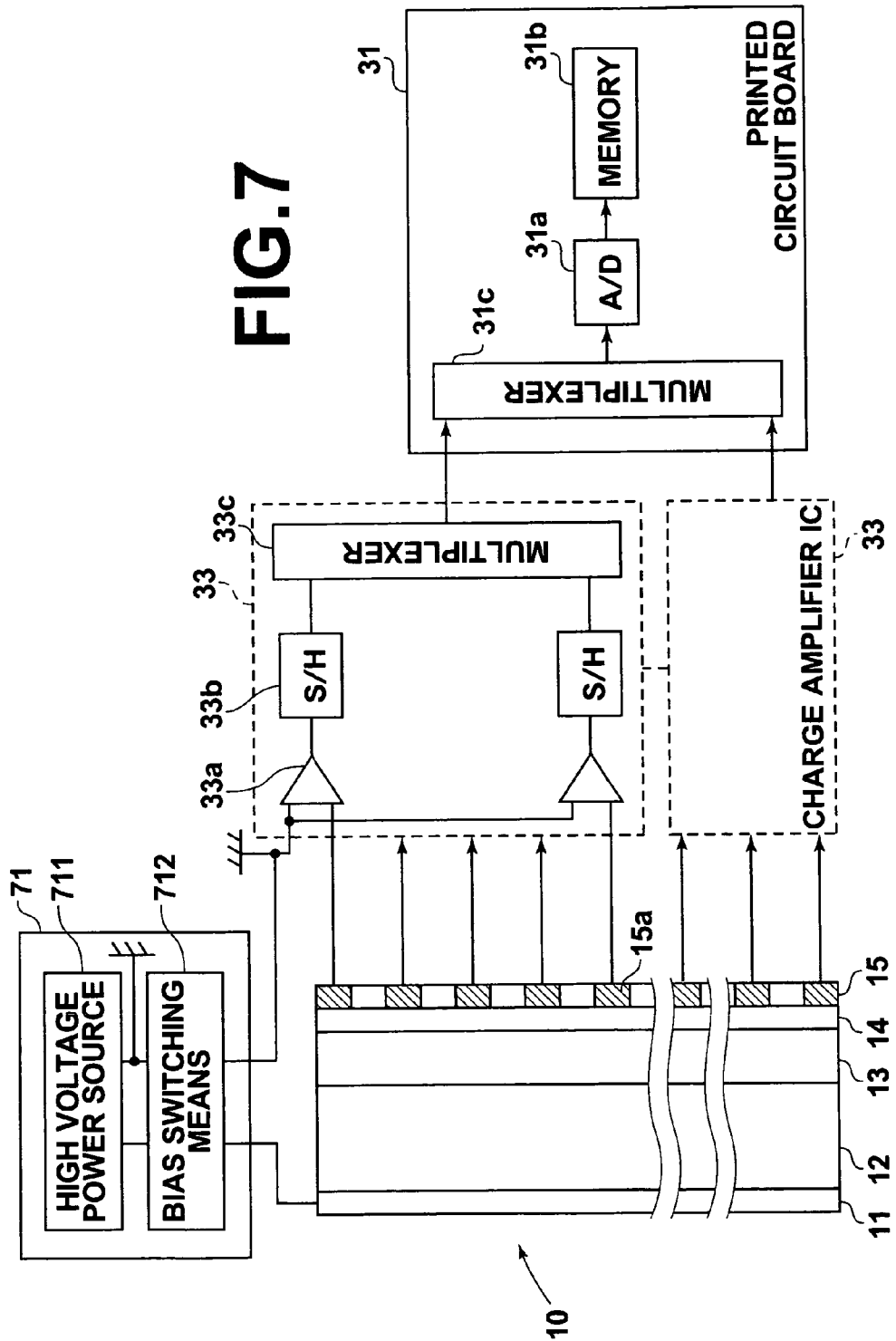
FIG. 7 is a block diagram illustrating the detail of the current detection means and high voltage power source, and the connection of the detection means and high voltage power source to the solid state detector.

FIG. 7 is a block diagram illustrating the detail of the current detection means 72 and high voltage power source section 71 provided in the object table 4, and the connection thereof to the solid state detector 10.

The high voltage power source section 71 is a circuit in which a high voltage power source 711 and a bias switching means 712 are integrated. The high voltage power source 711 is connected to the electrostatic recording section 10 through the bias switching means 712 that performs switching for applying a bias voltage to the electrostatic recording section 10, or shunting the recording section 10 to ground. The circuit is a charge/discharge surge current suppression design, in which a peak current that flows at the time of switching is limited to prevent the destruction of the sections of the apparatus where the currents are concentrated.

The charge amplifier IC 33 formed on the TAB film 32 includes: a number of charge amplifiers 33a, each connected to each element 15a of the solid state detector 10; a sample-and-hold (S/H) circuit 33b connected to each charge amplifier 33a; and a multiplexer 33c for multiplexing the signal outputted from each S/H circuit. The current flowing out of the solid state detector 10 is converted by each charge amplifier 33a to a voltage, which is sampled and held by the S/H circuit 33b at a predetermined timing. The voltage sampled and held by each S/H circuit, which corresponds to each element 15a, is sequentially outputted from the multiplexer 33c so as to be switched in the arrangement order of the elements 15a (corresponding to a part of the main scanning). The signals sequentially outputted from the multiplexer 33c are inputted to a multiplexer 31c provided on the printed circuit board 31, and the voltage corresponding to each element 15a is sequentially outputted from the multiplexer 31c so as to be switched in the arrangement order of the elements 15a, thereby the main scanning is completed. The signals sequentially outputted from the multiplexer 31c are converted to digital signals by an A/D converter 31c, and stored in a memory 31b.

As for the pre-exposure light source section 60, a light source that illuminates/extinguishes in a short time with very little afterglow is required. In the present embodiment, therefore, an external electrode type rare gas fluorescent lamp is used. More specifically, as shown in FIG. 4, the pre-exposure light source section 60 includes: a plurality of external electrode type rare gas fluorescent lamps 61 extending in the direction perpendicular to the surface of the drawing; a wavelength selection filter 62 provided between the florescent lamps and solid state detector 10; and a reflector 63 for reflecting light emitted from the fluorescent lamps 61 to the solid state detector 10 effectively. The pre-exposure light needs just to be irradiated on the entire surface of the second electrode layer 15, and a particular condenser means is not required, but a narrow luminance distribution is desirable. As for the light source, for example, LED chips disposed two dimensionally may be used instead of the fluorescent lamps.

The moving means 70 is constituted by a linear motor or the like (not shown), and reciprocally translates the solid state detector 10 between the imaging position and readout position.

In the present embodiment, an optical readout type solid state detector is used as the flat panel detector as an example. Alternatively, a TFT readout type solid state detector may also be used as the flat panel detector as described, for example, in Japanese Unexamined Patent Publication Nos. 2004-80749, 2004-73256. In the TFT readout type solid state detector, the signal charges stored in the storage section of the solid state detection element are read out by scan driving the TFTs connected to the storage section.

The dose detector 20 is disposed under the solid state detector 10, and as the dose detector 20, for example, an AEC sensor in which semiconductor detectors are disposed as the sensor for measuring the dose of radiation may be used. Alternatively, the dose detector 20 may be adapted to detect the dose of radiation irradiated on the solid state detector 10 (or TFT type flat panel detector). Hereinafter, in the present embodiment, the dose detector 20 will be described as the AEC sensor.

The dose detecting position changing means 21 moves the dose detector 20 parallel to the solid state detector 10 along the side of the object table 4 facing the chest wall H using a pulse motor or the like to change the position for detecting the dose of radiation.

Hereinafter, the operation of the mammography apparatus 1 constructed in the manner as described above will be described with reference to the case in which a breast image of a subject is obtained by MLO imaging.

Breasts are solid having a certain thickness, so that if the breast is imaged directly, a tumor may not be imaged due to interference by the mammary glands, fat, blood vessels, and the like. Therefore, in the mammography screening, the breast is clamped by the compression paddle 7 to stretch it thinly so that the shadow of any small lump is clearly imaged with a small amount of radiation. In order to compress the breast evenly, it is necessary to uniformly apply a pressure thereto. If a large compression paddle 7 is used for a small breast, a gap is developed around the breast, causing the compression paddle 7 to be inclined, and thereby the breast is not compressed evenly. Thus, it is necessary to use a compression paddle 7 having an appropriate size for the breast to be imaged.

Further, if a large compression paddle is used for a small breast, the back of the operator's hand is compressed onto the object table by a large area of the plate, causing the operator difficulty to withdraw its hand after positioning the breast.

Therefore, when imaging a breast of a subject, the operator selects an appropriate compression paddle 7 according to the size of the breast, and attaches to the mounting section 51 of the arm 5. When the selected compression paddle 7 is attached to the mounting section 51 of the mammography apparatus 1, the size of the compression paddle 7 is detected by the compression paddle size detection means 53.

Figure 8A:
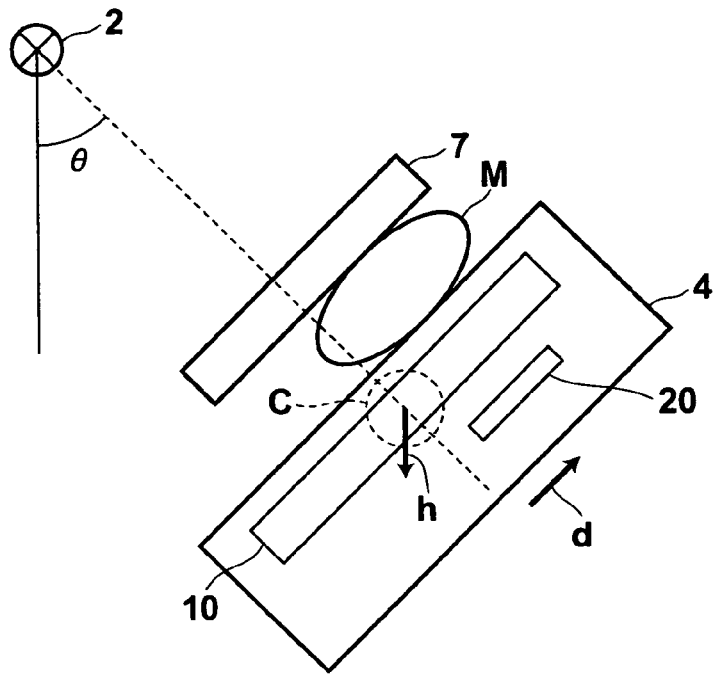
FIGS. 8A, 8B are drawings illustrating that the position of the dose detector is moved to the center of a breast.
Figure 8B:
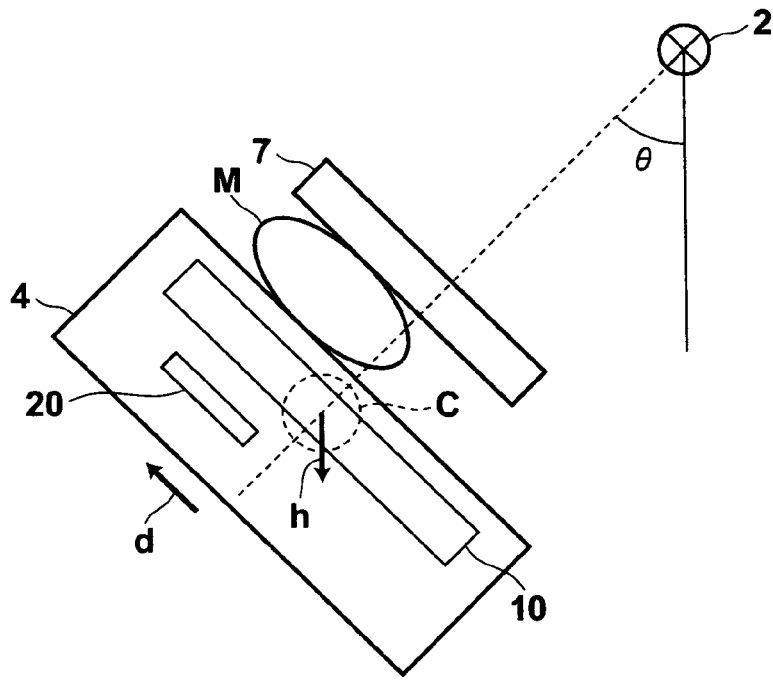

When a subject stands on the side of the mammography apparatus 1, the operator inputs the height of the object table 4 according to the height of the subject, and the arm 5 is adjusted by the object table height adjusting means 92 of the arm moving means 9 until the height of the object table 4 becomes the inputted height. Further, the operator inputs the angle of rotation of the arm 5 from the operation section 8 according to the size and shape of the breast of the subject, and the arm 5 is rotated by the arm rotation means 91 until the angle of rotation of the arm 5 becomes the inputted angle of rotation. Here, object table 4 is inclined at an angle in the range from 45 to 80 degrees from the horizontal direction of the object table so that the object table 4 becomes parallel to the chest muscles of the subject. Generally, the object table 4 is inclined around 60 degrees from the horizontal direction for imaging. Depending on which of the right or left breast is imaged, the direction of inclination of the object table is different as shown in FIGS. 8A, 8B (FIG. 8A for right breast, FIG. 8B for left breast).

Imaging is performed with the upper side of the inclined object table 4 contacted with the chest muscle. Therefore, if a small breast is imaged on the object table for large breast, the center of the breast does not correspond to the center of the object table 4, being always displaced to either side, as shown in FIGS. 8A, 8B. In order to obtain a breast image having an appropriate density with a small amount of radiation exposure, it is necessary to measure the dose of radiation transmitted through the central portion of the breast by the AEC sensor 20, the dose of radiation is not detected correctly for the small breast displaced from the center of the object table 4.

Consequently, the radiation dose measuring means moves the AEC sensor, which detects the dose of radiation irradiated from the radiation irradiation section and reached the object table 4, to a position on the straight line passing through the radiation irradiation section 3 and center of the breast M.

First, the size of the breast is determined by the breast size detection means based on the size of the compression paddle 7 detected by the compression paddle size detection means 53. If the size of the compression paddle 7 is small, the size of the breast M of the subject is determined to be small. If the size of the compression paddle 7 is large, the size of the breast M of the subject is determined to be large.

When a small breast is imaged, the breast is recorded with its position displaced to either side (FIGS. 8A, 8B). But, the direction of rotation of the arm 5 differs depending on which of the right or left breast M is imaged. Therefore, the displaced direction of the breast from the center of the object table 4 may be known according to the direction of rotation of the arm 5. Thus, the position of the breast M of the subject placed on the object table 4 is detected by a breast position detection means based on the size of the breast detected by the breast size detection means, and the direction of rotation of the arm 5 rotated by the arm rotation means 91. If the size of the breast M is large, the breast is assumed to be placed adjacent to the center of the object table, and if the size of the breast M is small, the breast is assumed to be displaced from the center of the object table 4 always by a distance d.

According to the position of the breast M detected by the breast position detection means, the radiation dose measuring means moves the AEC sensor 20 by the dose detecting position changing means 21 and measures the dose of radiation transmitted through the center of the breast and reached the object table 4. The breast size detection means determines that the breast of the subject is small if the size of the compression paddle 7 detected by the compression paddle size detection means 53 is small, and causes the dose detecting position changing means 21 to move the position of the AEC sensor 20 by a predetermined distance d along the side of the object table 4 facing the chest wall H (long side directions) so that the AEC sensor 20 is placed at a position corresponding to the central portion of the breast. The distanced d is, for example, around 3 cm, which corresponds to ½ of the difference in length between the long side of the large compression paddle and that of the small compression paddle. The direction of the angle of rotation θ of the arm 5 differs depending on which of the right or left breast is to be imaged, so that the moving direction of the AEC sensor is reversed according to the direction of rotation (or angle of rotation θ).

When imaging is performed on the inclined object table 4 with the upper side thereof contacted with the chest muscle H, the imaging position becomes higher by an amount of h as the object table 4 is inclined further as shown in FIGS. 8A, 8B. Therefore, the arm 5 is moved downward by the amount of h through the arm moving means 9. This reduces the effort of the operator and burden on the subject.

The amount of h may be obtained by the following formula, when the travel distance of the AEC sensor is d, and the inclination of the arm 5 is θ.

$$h = d \times \cos\theta$$

After the object table 4 is inclined to an optimum angle for imaging, the breast is compressed by the compression paddle.

Checking the pressurized state of the breast, the operator inputs an instruction to gradually increase the pressure on the breast through the operation panel, foot switch, or the like. Then, according to the inputted instruction, the compression paddle moving means 52 gradually presses down the compression paddle 7 in the longitudinal direction of the arm 5. For example, the pressing pressure is increased by 1 kg every time the foot switch is depressed, and the foot switch is depressed continuously until the thickness of the breast becomes appropriate for imaging. Alternatively, a configuration may be adopted in which the compression paddle gradually increases the pressure after it is moved downward and touched on the breast.

After the pressing process is completed, radiation is irradiated from the radiation source 2 of the radiation irradiation section 3, and the imaging is performed.

In the present embodiment, description has been made of a case in which the size of a breast is determined according to the size of the compression paddle. But, the size of the breast may also be detected by pre-exposing the breast with a small amount of radiation by the breast size detection means prior to imaging. More specifically, for example, since the pixel value differs between the breast area and directly exposed area by the radiation in an image obtained by the solid state detector 10 through the pre-exposure, the breast area may be extracted through binarization of the image using a predetermined threshold value, and the size of the breast may be determined based on the number of pixels in the extracted breast area and the edge length thereof on the side of the chest wall H. Any of the size and position detection can be based on a detected physical parameter represented by a computer processed signal. Some alternatives are described below.

Alternatively, the size of the breast may be detected from the image obtained just before or in the past.

When the size of the breast is detected through the pre-exposure, the size of the breast may be classified into a several levels according to the detected size of the breast, and a plurality of distances for moving the AEC sensor 20 may be provided according to the level.

Figure 15:
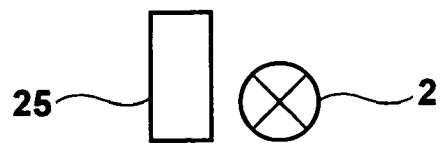
FIG. 15 is a drawing illustrating that a CCD camera is installed adjacent to the radiation irradiation section.
Figure 15:
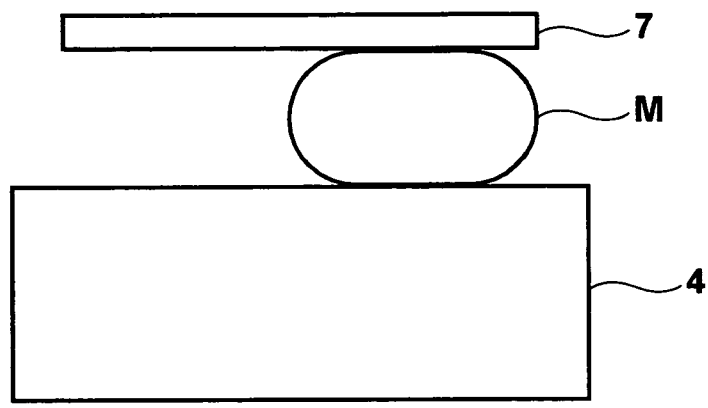

Alternatively, as shown in FIG. 15, a CCD camera may be installed adjacent to the radiation irradiation section 2 as the breast size detection means to image the compressed breast, and the size of the breast area may be detected from the image obtained by the CCD camera 25. Further, the size of the breast area maybe obtained by irradiating ultrasonic waves on the breast, and receiving the reflected waves. These methods may detect the size of the breast without exposing the subject to radiation. Further, a subtle movement of the compression paddle for aligning with the center of the breast may be realized. Still further, a configuration may be adopted in which even if a large compression paddle is attached by mistake by the operator, the compression paddle is moved so as to be aligned with the center of the breast, or an alert for changing the compression paddle is issued if the improper compression paddle is attached.

Further, a strain gauge may be provided in the object table 4, and the size of the breast may be detected by calculating the weight of the breast based on the reading of the strain gauge. Still further, the size of the breast may be detected from an image examined by using ultrasonic waves immediately preceding the mammography imaging.

Figure 16:
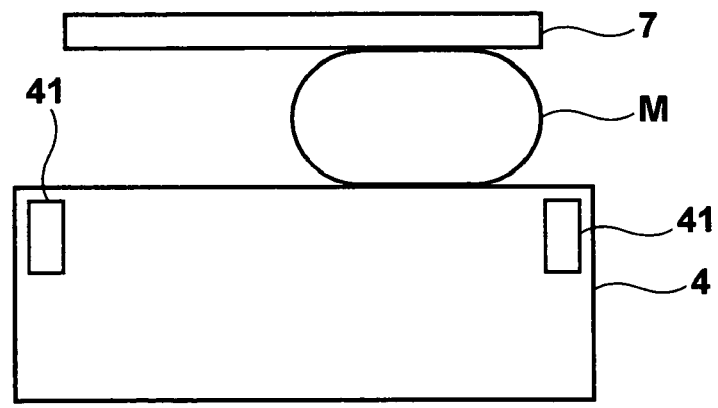
FIG. 16 is a drawing illustrating that a strain gauge is provided in the object table.

In the embodiment above, the description has been made of a case in which the position of the breast M is detected by the breast position detection means based on the size of the breast detected by the breast size detection means and the direction of rotation of the arm 5 rotated by the arm moving means. But, a configuration may be adopted in which a strain gauge 41 is provided on each side of the object table 4 as shown in FIG. 16, and the position of the breast M may be determined by checking the balance between the outputs of the strain gauges. If a pressure is applied on the object table 4, a strain is developed, thereby the resistance value of the strain gauge 41 is changed according to the strain. Thus, the position of the breast placed on the object table 4 may be determined from the difference in the output between the two strain gauges 41. For example, the position of a breast may be expressed by the following Formula, using a difference in the output between the two strain gauges 41 and a pressing pressure applied on the compression paddle.

Breast Position=fx(pressing pressure, difference in the output between the two strain gauges)

Further, a configuration may be adopted in which a temperature sensor is provided on the side of the object table 4 facing the chest wall H, and the position of the breast is detected from the position where the subject is contacting the object table 4.

When performing MLO imaging, the position of the breast M placed on the object table 4 may be determined based on the height of the object table 4 adjusted by the object table height adjusting means 92. When performing MLO imaging, the object table 4 is inclined through rotating the arm 5 by the arm rotation means 91 for imaging. In addition, if the subject is tall, the object table 4 is moved upward since the position of the breast is relatively high. In this case, the distance from the underarm to the center of the breast is also relatively large, so that the breast M may be placed at a position adjacent to the center of the inclined object table 4. But, if the subject is small, the breast M is not placed at a position adjacent to the center of the object table 4 but at a position slightly displaced upward from the center. Thus, a table like that shown in FIG. 17 may be provided for MLO imaging based on the measuring results of the correspondence between the height of the object table 4 and the position of the breast M of the subject obtained in advance, and according to the table, the height of the object table 4 and the approximate position of the breast M displaced from the center of the object table 4 may be determined. Then, the radiation irradiation section 2 or the object table 4 may be moved based on the value in the table.

Further, if the breast M is large, imaging is performed with the object table inclined relatively small, but if the breast M is small, imaging is performed with the object table 4 inclined close to the vertical. Accordingly, the position of the breast M may also be determined according to the inclination of the object table 4.

Figures 17, 18:
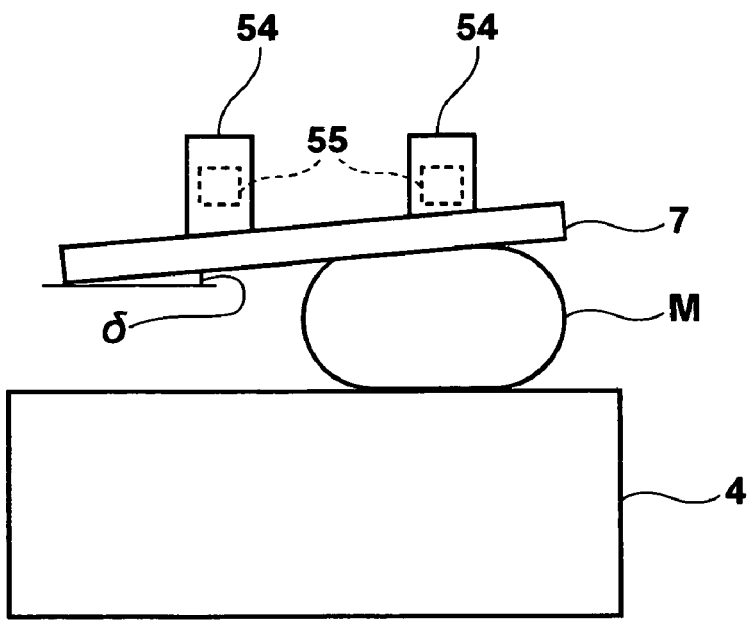
FIG. 17 is a drawing illustrating the relationship between the height of the object table and the position of a breast.
FIG. 18 is a drawing illustrating the relationship between the inclination of the compression paddle and the position of a breast.

Still further, when the breast M placed on the object table 4 is compressed by the compression paddle 7, if the breast M is small, it is displaced to either side, so that the pressurized compression paddle 7 and the object table 4 are not aligned in parallel, and the pressurized compression paddle 7 is inclined slightly with reference to the object table 4, as shown in FIG. 18. By detecting such inclination, the approximate position of the breast M on the object table may be determined. Thus, a compression paddle inclination detection means 55 for detecting an inclination angle δ of the compression paddle 7 with reference to the object table 4 may be provided on the insertion section of the compression paddle 7 or the like, and the position of the breast M on the object table may be determined by the breast position detection means according to the inclination angle of the compression paddle 7. More specifically, the displacement of the breast M may be detected from the stress of the two insertion section 54 supporting the compression paddle 7.

If the compression paddle 7 is provided such that it is not inclined with reference to the object table 4, the position of the breast M may be determined only from the distribution of the stresses incurred by the compression paddle 7 or the object table 4.

Figure 19:
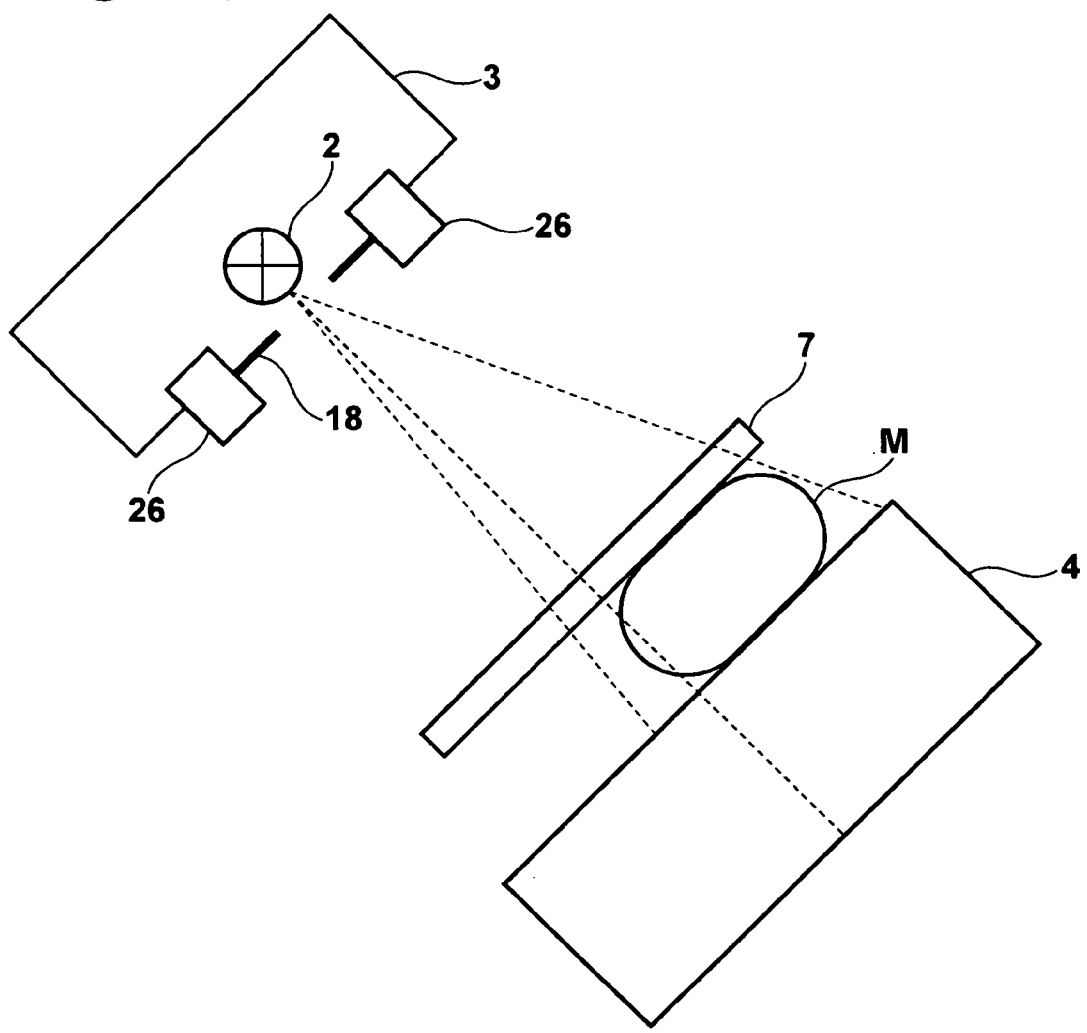
FIG. 19 is a drawing illustrating the relationship between the radiation field aperture and the position of a breast.

Further, if imaging is performed by attaching a radiation field aperture 18 to the radiation accommodation section 3 having therein the radiation irradiation section 2, as shown in FIG. 19, the radiation field aperture 18 is attached such that the breast M is placed at the center of the image. Thus, a radiation field aperture detection means 26 capable of detecting the position of the radiation field aperture 18 using a dial for adjusting the radiation field size of the side of the object table 4 facing the chest wall H or the side orthogonal to the side facing the chest wall H may be provided at the mounting section of the radiation field aperture 18 of the radiation accommodation section 3, and the position of the breast M on the object table may be determined according to the position of the radiation field aperture 18 attached to the radiation accommodating section 3.

The foregoing description has been made of a case in which the AEC sensor is moved such that the dose of radiation irradiated from the radiation irradiation section and reached the object table transmitted through the center of the breast is detected. The AEC sensor may be moved such that the dose of radiation transmitted through the target region (region of interest) and reached the object table is detected to optimize the recorded image.

Figure 10:
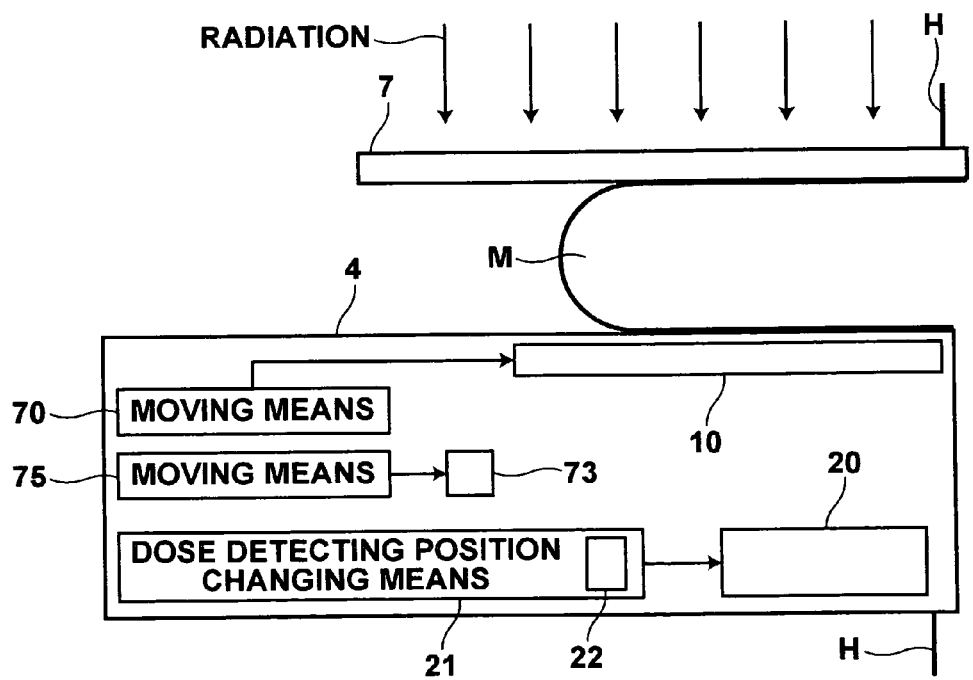
FIG. 10 is a drawing illustrating the relationship among the compression paddle, solid state detector, and dose detector (example 2).

Further, a first switching means 22 for switching whether to move the position of the dose detector according to the size detected by the compression paddle size detection means 53 may be provided in the dose detecting position changing means 21 as shown in FIG. 10. Then, the moving function for moving the AEC sensor 20 is switched off if the size of the compression paddle 7 detected by the compression paddle size detection means 53 is large, and the moving function for moving the AEC sensor 20 is switched ON only when the size of the compression paddle 7 detected by the compression paddle size detection means 53 is small.

Figure 9:
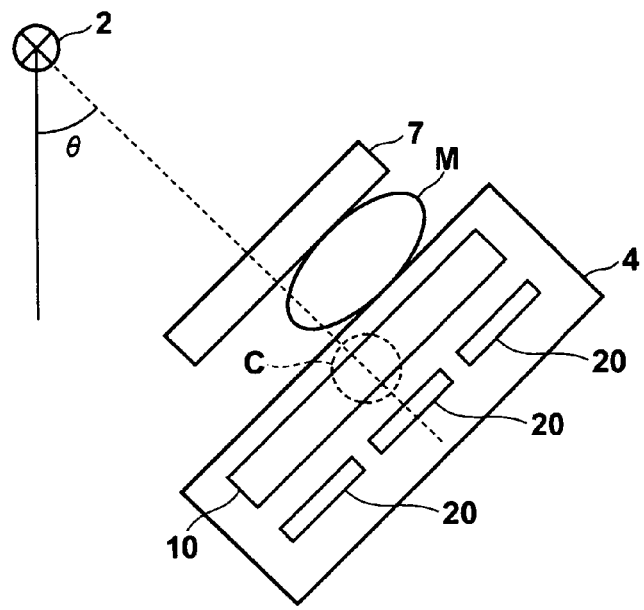
FIG. 9 is a schematic view of an object table having a plurality of dose detectors.

Still further, in the present embodiment, a single AEC sensor is used. But, if a plurality of AEC sensors is arranged along the side of the object table 4 facing the chest wall as shown in FIG. 9, the dose detecting position changing means 21 may be a dose detecting position selection means for selecting one of the plurality of sensors 20.

Figure 20:
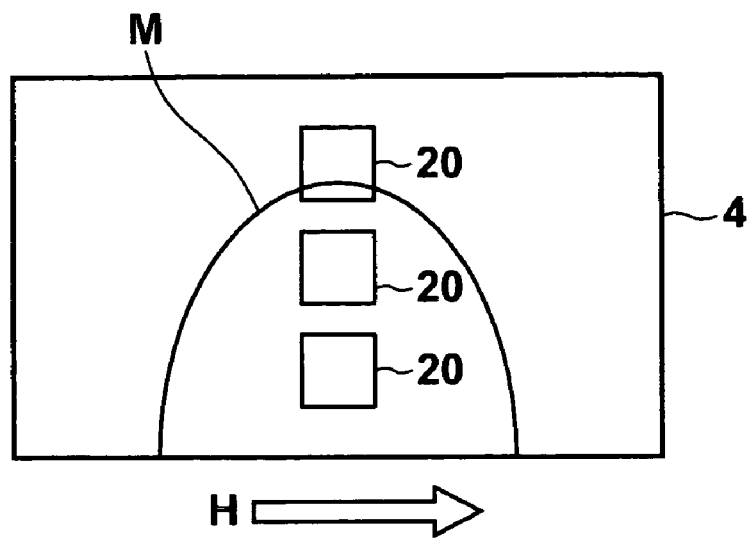
FIG. 20 is a drawing illustrating the object table having a plurality of dose detectors arranged in the direction away from the chest wall.

Further, as shown in FIG. 20 (a drawing of the object table 4 viewed from the side from which a breast is placed), a configuration may be adopted in which several AEC sensors 20 are arranged in the direction away from the side of the object table 4 facing the chest wall H, and the dose detecting position changing means 21 selects one of the AEC sensors and moves the position of the selected AEC sensor 20 along the side of the object table 4 facing the chest wall H (arrow direction in FIG. 20).

As described above in detail, by moving the AEC sensor to detect the dose of radiation at the center of the breast, an image having an optimum density may be obtained with a reduced amount of radiation exposure to the subject.

Figure 21:
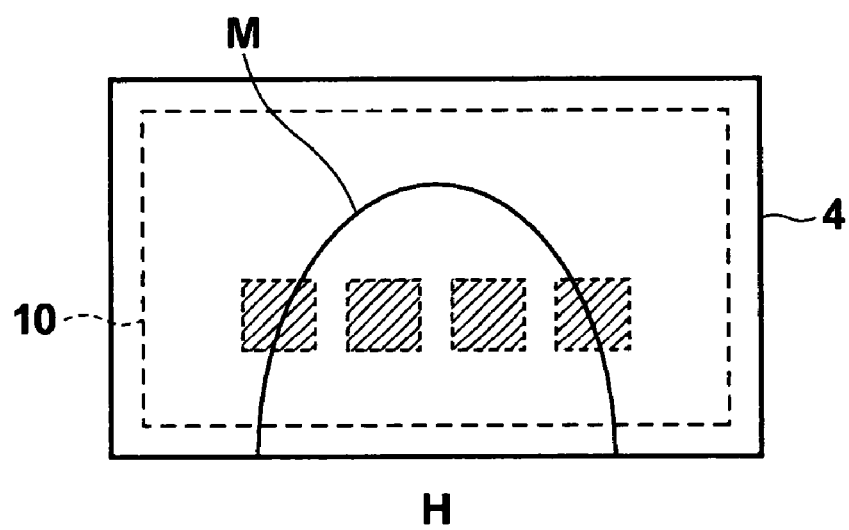
FIG. 21 is a drawing illustrating the regions of the flat panel detector used for detecting the dose of radiation.

Further, a configuration may be adopted in which the flat panel detector 10 is used for detecting the does of radiation instead of the AEC sensor, in which some of the segmented regions (shaded regions) of the detector 10 function as the dose detectors as shown in FIG. 21, and one of the segmented region is selected by the dose detecting position selection means to detect the dose of radiation.

Figure 11:
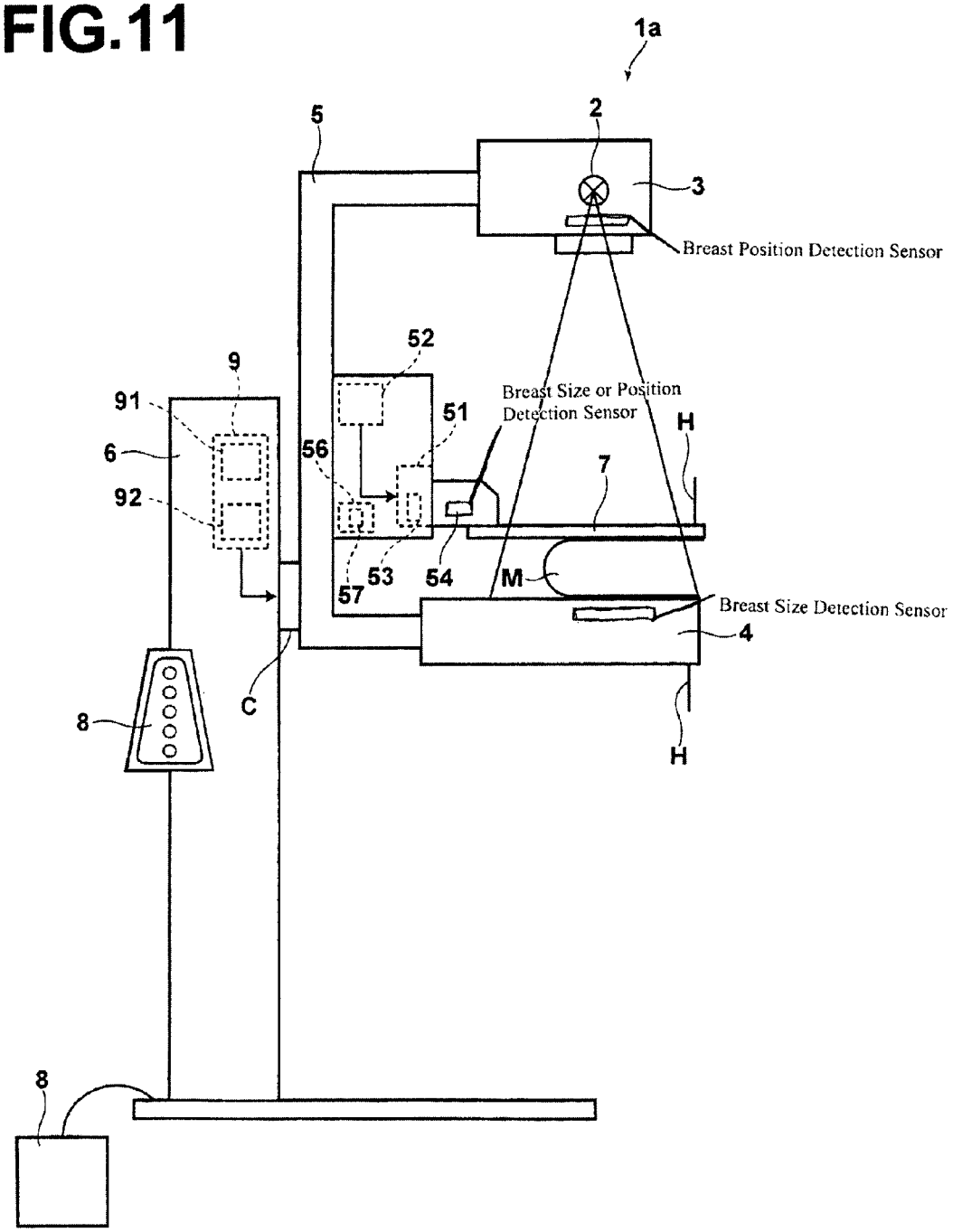
FIG. 11 is a schematic view of the mammography apparatus according to a second embodiment of the present invention.

Hereinafter, a second embodiment of the present invention will be described. In the second embodiment, elements identical to those used in the first embodiment are given the same reference numerals, and will not be elaborated upon further here. FIG. 11 is a schematic view of the mammography apparatus according to the second embodiment of the present invention. The mammography apparatus 1a of the present invention further includes a compression paddle compressing position moving means 56 in addition to the mammography apparatus 1 of the first embodiment.

In order to compress a breast evenly, it is necessary to uniformly apply pressure thereto. Although the small compression paddle 7 is used for a small breast, it is also desirable to compress a portion of the breast adjacent to the center thereof in order to compress the breast evenly.

Figure 12:
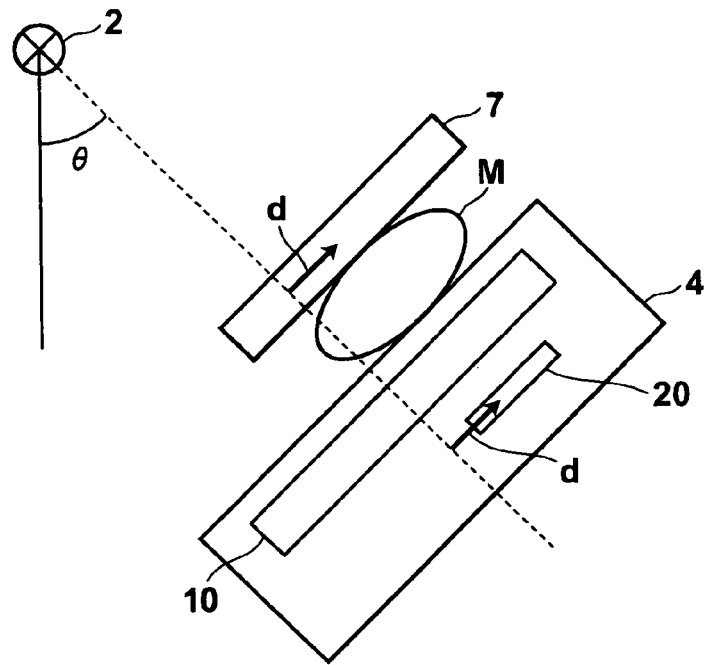
FIG. 12 is a drawing illustrating that the positions of the compression paddle and dose detector are moved to the center of a breast.

Therefore, as shown in FIG. 12, if the size of the compression paddle 7 detected by the compression paddle size detection means 53 is small, the AEC sensor 20 is moved so as to be positioned at a place corresponding to the central portion of the breast. In addition, the compression paddle 7 is moved by the compression paddle compressing position moving means 56 across the arm 5 along the side of the object table 4 facing the chest wall H by a distance d, which is substantially equal to the travel distance of the AEC sensor 20, so as to be positioned at a place corresponding to the central portion of the breast.

Further, a second switching means 57 for switching whether to move the position of the dose detector according to the size detected by the compression paddle size detection means 53 may be provided in the compression paddle compressing position moving means 56. Then, the moving function for moving the AEC sensor 20 is switched off if the size of the compression paddle 7 detected by the compression paddle size detection means 53 is large, and the moving function for moving the AEC sensor 20 is switched on only when the size of the compression paddle 7 detected by the compression paddle size detection means 53 is small.

Figure 13:
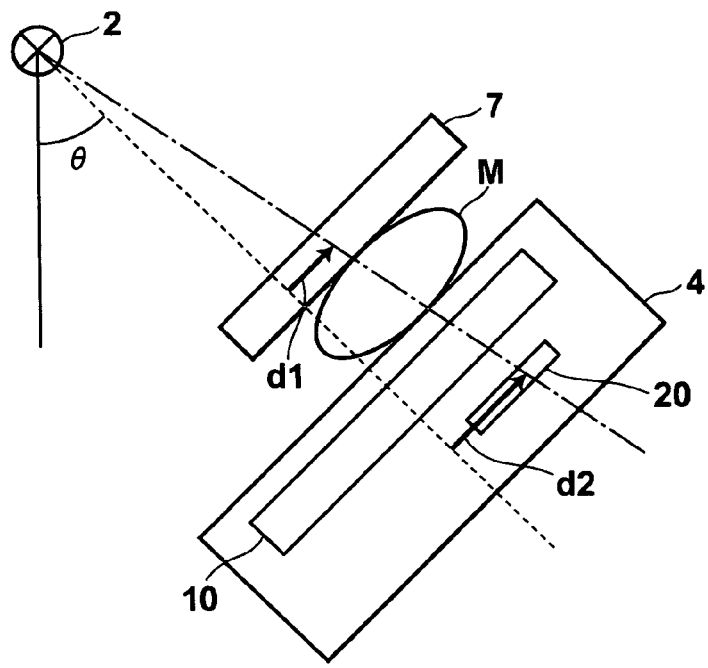
FIG. 13 is a drawing illustrating that the positions of the compression paddle and dose detector are moved by different amounts.
Figure 14A:
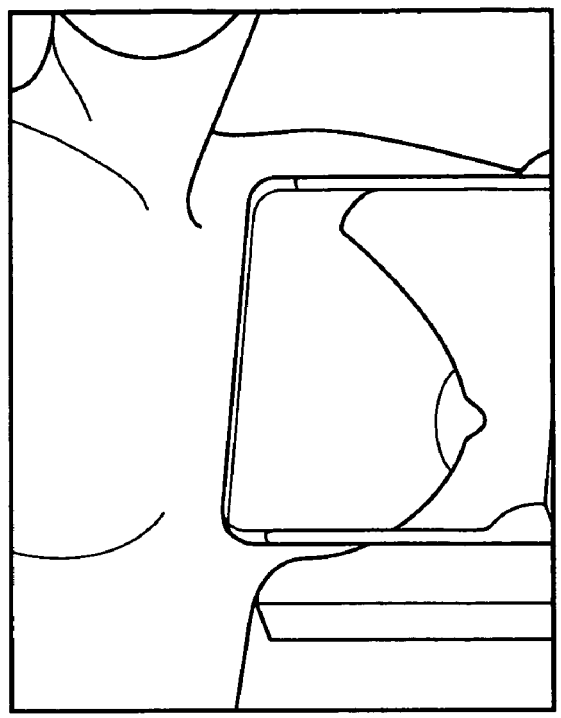
FIG. 14A is a drawing for explaining MLO imaging.
Figure 14B:
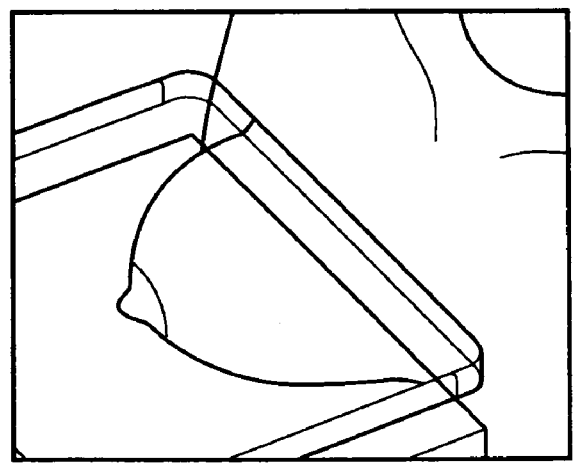
FIG. 14B is a drawing for explaining CC imaging.

As shown in FIG. 13, if the breast is small, the radiation emitted from the radiation source 2 and transmitted through the breast propagates in the direction indicated by the dash-dot line. Therefore, a configuration may be adopted in which the travel distance d2 of the AEC sensor 20 is greater than the travel distance d1 of the compression paddle 7.

In the present embodiment, both the AEC sensor and compression paddle 7 are moved, but a configuration may be adopted in which only the compression paddle 7 is moved.

As described above in detail, by moving the compression paddle such that the center thereof corresponds to the center of the breast, the breast may be compressed evenly.

Further, in each of the embodiments described above, description has been made of a case in which the spindle C, the rotation center of the arm 5, is attached to the arm at a position corresponding to the center of the flat panel detector. But if the center positions thereof are displaced with each other in consideration of the thickness of the breast, the travel distance of the arm in the upward or downward direction may be controlled taking into account the displaced distance.

Still further, in the embodiment described above, an AEC sensor is used as the dose detector, but the flat panel detector is also used as the dose detector. That is, the target X-ray intensity may be obtained by the flat panel detector through the pre-exposure. In this case, the region of the detector to be used as the AEC sensor may be selectively activated, the position of mammary glands may be detected by image recognition technique, and the weighting of the image regions may be changed when obtaining the X-ray intensity for this purpose.

What is claimed is:

1. A mammography apparatus, comprising:
    a radiation irradiation section for irradiating radiation on a breast of a subject;
    an object table having therein an image recording medium that receives the radiation to record image information thereon according to the dose of radiation transmitted through the breast, and a dose detector for detecting the dose of radiation irradiated from the radiation irradiation section and transmitted through the breast;
    an arm connecting the radiation irradiation section and object table such that they face each other;
    a compression paddle, disposed between the radiation irradiation section and object table, for compressing the breast onto the object table;
    an arm rotation means for rotating the arm according to the imaging direction for the breast;
    a breast size detection means for detecting the size of the breast of the subject; and
    a dose detecting position changing means for changing the dose detecting position of the dose detector along the side of the object table facing the chest wall of the subject according to the detected size of the breast and the direction of rotation of the arm when rotated by the arm rotation means.

2. The mammography apparatus according to claim 1, further comprising a compression paddle compressing position moving means for moving the compressing position of the compression paddle along the side of the object table facing the chest wall of the subject according to the detected size of the breast and the direction of rotation of the arm when rotated by the arm rotation means.

3. The mammography apparatus according to claim 1, wherein:
    the apparatus further comprises a compression paddle size detection means for detecting the size of the compression paddle; and
    the breast size detection means detects the size of breast corresponding to the detected size of the compression paddle as the size of the breast of the subject.

4. The mammography apparatus according to claim 3, wherein the compression paddle compressing position moving means includes a second switching means for switching whether to move the compressing position of the compression paddle according to the detected size of the compression paddle.

5. The mammography apparatus according to claim 3, wherein the dose detecting position changing means includes a first switching means for switching whether to move the dose detecting position of the dose detector according to the detected size of the compression paddle.

6. The mammography apparatus according to claim 1, wherein the breast size detection means detects the size of the breast of the subject from the image information recorded on the image recording medium.

7. The mammography apparatus according to claim 2, wherein the breast size detection means detects the size of the breast of the subject from the image information recorded on the image recording medium.

8. A mammography apparatus, comprising:
    a radiation irradiation section for irradiating radiation on a breast of a subject;
    an object table having therein an image recording medium that receives the radiation to record image information thereon according to the dose of radiation transmitted through the breast, and a dose detector for detecting the dose of radiation irradiated from the radiation irradiation section and transmitted through the breast;
    an arm connecting the radiation irradiation section and object table such that they face each other;
    a compression paddle, disposed between the radiation irradiation section and object table, for compressing the breast onto the object table;
    an arm rotation means for rotating the arm according to the imaging direction for the breast;
    a breast size detection means for detecting the size of the breast on the object table; and
    a compression paddle compressing position moving means for moving a compressing position of the compression paddle along the side of the object table facing the chest wall of the subject according to the detected size of the breast and an angle of rotation of the arm when rotated by the arm rotation means.

9. The mammography apparatus according to claim 8, wherein:
    the apparatus further comprises a compression paddle size detection means for detecting the size of the compression paddle; and
    the breast size detection means detects the size of breast corresponding to the detected size of the compression paddle as the size of the breast of the subject.

10. The mammography apparatus according to claim 9, wherein the compression paddle compressing position moving means includes a second switching means for switching whether to move the compressing position of the compression paddle according to the detected size of the compression paddle.

11. The mammography apparatus according to claim 8, wherein the breast size detection means detects the size of the breast of the subject from the image information recorded on the image recording medium.

12. A mammography apparatus, comprising
    a radiation irradiation section for irradiating radiation on a breast of a subject;
    an object table for placing the breast thereon;
    a breast position detection means for detecting the position of the breast on the object table along the side of the object table facing the chest wall of the subject;
    a radiation dose measuring means for measuring the dose of radiation irradiated from the radiation irradiation section and reached the object table at a position on the straight line passing through the radiation irradiation section and region of interest of the breast based on the position of the breast detected by the breast position detection means.

13. The mammography apparatus according to claim 12, wherein the radiation dose measuring means comprises:
    a plurality of dose detectors arranged along the side of the object table facing the chest wall; and
    a dose detecting position selection means for selecting the dose detector located on the straight line passing through the radiation irradiation section and region of interest of the breast.

14. The mammography apparatus according to claim 12, wherein the radiation dose measuring means comprises:
    a dose detector provided movably along the side of the object table facing the chest wall; and
    a dose detecting position changing means for changing the dose detecting position by moving the dose detector to a position on the straight line passing through the radiation irradiation section and region of interest of the breast.

15. The mammography apparatus according to claim 12, wherein:

the apparatus further comprises:
- an arm connecting the radiation irradiation section and object table such that they face each other;
- an arm rotation means for rotating the arm according to the imaging direction for the breast; and
- a breast size detection means for detecting the size of the breast of the subject; and the breast position detection means detects the position of the breast on the object table according to the angle of rotation of the arm when rotated by the arm rotation means and the size of the breast.

16. The mammography apparatus according to claim 12, wherein:

the apparatus further comprises an object table height adjusting means for adjusting the height of the object table; and the breast position detection means determines the position of the breast on the object table according to the height of the object table adjusted by the object table height adjusting means.

17. The mammography apparatus according to claim 12, wherein:

the apparatus further comprises:
- a compression paddle, disposed between the radiation irradiation section and object table, for compressing the breast onto the object table; and
- a compression paddle inclination detection means for detecting an inclination angle of the compression paddle formed with respect to the object table while the breast is clamped between the compression paddle and the object table and compressed; and the breast position detection means determines the position of the breast on the object table according to the inclination angle of the compression paddle.

18. The mammography apparatus according to claim 12, wherein:

the apparatus further comprises a radiation field aperture detection means for detecting the position where a radiation field aperture for the radiation irradiation section is attached; and the breast position detection means determines the position of the breast on the object table according to the position of the radiation field aperture.

19. A mammography apparatus, comprising:
- a radiation irradiation section for irradiating radiation on a breast of a subject;
- an object table for placing the breast thereon;
- an arm connecting the radiation irradiation section and object table such that they face each other;
- a compression paddle, disposed between the radiation irradiation section and object table, for compressing the breast onto the object table;
- a breast position detection means for detecting the position of the breast on the object table along the side of the object table facing the chest wall of the subject; and
- a compression paddle compressing position moving means for moving a compressing position of the compression paddle along the side of the object table facing the chest wall of the subject based on the position of the breast detected by the breast position detection means.

20. The mammography apparatus according to claim 19, wherein:

the apparatus further comprises:
- an arm rotation means for rotating the arm according to the imaging direction for the breast; and
- a breast size detection means for detecting the size of the breast on the object table; and the breast position detection means detects the position of the breast on the object table according to the angle of rotation of the arm when rotated by the arm rotation means and the size of the breast.

21. The mammography apparatus according to claim 19, wherein:

the apparatus further comprises an object table height adjusting means for adjusting the height of the object table; and the breast position detection means determines the position of the breast on the object table according to the height of the object table adjusted by the object table height adjusting means.

22. The mammography apparatus according to claim 19, wherein:

the apparatus further comprises a compression paddle inclination detection means for detecting an inclination angle of the compression paddle formed with respect to the object table while the breast is clamped between the compression paddle and the object table and compressed; and the breast position detection means determines the position of the breast on the object table according to the inclination angle of the compression paddle.

23. The mammography apparatus according to claim 19, wherein:

the apparatus further comprises a radiation field aperture detection means for detecting the position where a radiation field aperture for the radiation irradiation section is attached; and the breast position detection means determines the position of the breast on the object table according to the position of the radiation field aperture.

* * * * *